(12) United States Patent
Kim

(10) Patent No.: US 10,843,897 B2
(45) Date of Patent: Nov. 24, 2020

(54) EMERGENCY ELEVATOR

(71) Applicant: Songsan Special Elevators Co., Ltd., Gyeonggi-do (KR)

(72) Inventor: Gi-Young Kim, Gyeonggi-do (KR)

(73) Assignee: SONGSAN SPECIAL ELEVATORS CO., LTD., Gyeonggi-Do (KR)

( * ) Notice: Subject to any disclaimer, the term of this patent is extended or adjusted under 35 U.S.C. 154(b) by 307 days.

(21) Appl. No.: 15/993,295

(22) Filed: May 30, 2018

(65) Prior Publication Data
US 2019/0367324 A1    Dec. 5, 2019

(51) Int. Cl.
| | |
|---|---|
| B66B 5/00 | (2006.01) |
| B66B 5/02 | (2006.01) |
| B66B 11/02 | (2006.01) |
| B66B 13/30 | (2006.01) |
| A62B 7/08 | (2006.01) |

(Continued)

(52) U.S. Cl.
CPC .................. *B66B 5/00* (2013.01); *A61L 9/20* (2013.01); *A62B 7/08* (2013.01); *A62B 7/10* (2013.01); *A62B 11/00* (2013.01); *A62B 18/02* (2013.01); *A62C 3/00* (2013.01); *B01D 46/0028* (2013.01); *B01D 53/04* (2013.01); *B66B 5/02* (2013.01); *B66B 5/027* (2013.01); *B66B 11/024* (2013.01); *B66B 11/0233* (2013.01); *B66B 13/308* (2013.01); *B01D 2253/102* (2013.01); *B01D 2259/4508* (2013.01); *B01D 2279/50* (2013.01)

(58) Field of Classification Search
CPC .. B66B 5/00; B66B 5/024; B66B 5/02; B66B 5/027; B66B 11/024; B66B 13/306; B66B 13/308; B66B 13/303; B66B 13/08; B66B 13/30; A61L 9/20; A62B 18/02; A62B 11/00; A62B 7/08
See application file for complete search history.

(56) References Cited

U.S. PATENT DOCUMENTS 1,848,136 A * 3/1932 Meissner .............. E05F 15/619
318/256
4,042,066 A * 8/1977 Noone ..................... A62B 1/02
182/142

(Continued)

FOREIGN PATENT DOCUMENTS

| CN | 105064854 | * 11/2015 |
| CN | 107697775 | * 2/2018 |

(Continued)

*Primary Examiner* — Rachel T Sippel
*Assistant Examiner* — Kelsey E Baller

(57) ABSTRACT

An emergency elevator includes a door frame installed on upper, left and right sides of an entrance of an elevator platform, an elevator car configured to vertically move along an elevator passage and provided with a pair of elevator doors, a pair of platform doors installed in the door frame, a lower frame installed on a lower side of the entrance of the elevator platform and configured to slidably support the platform doors, an upper door rim installed on an upper side of the platform doors, a side door rim vertically installed at a lateral end of the platform doors, an oxygen supply device configured to supply oxygen to a patient in the elevator car, an emergency ventilation device configured to supply a purified air into the elevator car, and a filter device provided in the blowing duct so as to remove harmful substances introduced into the elevator car.

17 Claims, 13 Drawing Sheets

(51) Int. Cl.
  *A62B 7/10*    (2006.01)
  *A62B 11/00*   (2006.01)
  *A62B 18/02*   (2006.01)
  *B01D 46/00*   (2006.01)
  *B01D 53/04*   (2006.01)
  *A62C 3/00*    (2006.01)
  *A61L 9/20*    (2006.01)

(56) References Cited

U.S. PATENT DOCUMENTS

| | | | | |
|---|---|---|---|---|
| 5,033,489 | A * | 7/1991 | Ferre | B60S 3/002 |
| | | | | 134/107 |
| 5,165,505 | A * | 11/1992 | Hayashi | B66B 13/08 |
| | | | | 187/333 |
| 5,354,233 | A * | 10/1994 | Mandy | B66B 11/024 |
| | | | | 187/393 |
| 5,673,770 | A * | 10/1997 | Friedman | B66B 13/08 |
| | | | | 187/333 |
| 5,837,040 | A * | 11/1998 | Caughron | B01D 46/0023 |
| | | | | 96/224 |
| 6,948,592 | B2 * | 9/2005 | Kavounas | A61N 1/39 |
| | | | | 187/384 |
| 9,598,265 | B1 * | 3/2017 | Jacobs | E05F 15/619 |
| | | | | 318/256 |
| 2005/0224299 | A1 * | 10/2005 | Soemardjan | B66B 11/0246 |
| | | | | 187/406 |
| 2005/0284168 | A1 * | 12/2005 | Lee | F24F 1/0007 |
| | | | | 62/317 |
| 2011/0008742 | A1 * | 1/2011 | Katsumata | F27D 15/02 |
| | | | | 432/36 |
| 2013/0312744 | A1 * | 11/2013 | Kshirsagar | B64D 11/00 |
| | | | | 128/202.26 |
| 2014/0069827 | A1 * | 3/2014 | Thede | B65D 85/00 |
| | | | | 206/223 |

FOREIGN PATENT DOCUMENTS

| | | | | |
|---|---|---|---|---|
| CN | 109179160 | * | 1/2019 | |
| EP | 1044920 A2 | * | 10/2000 | B66B 13/303 |
| JP | 2005106296 | * | 4/2005 | |
| JP | 2006137584 A | | 6/2006 | |
| JP | 2014516894 A | | 7/2014 | |
| JP | 2016124631 A | | 7/2016 | |
| KR | 20040003887 A | | 1/2004 | |
| KR | 20080085964 A | | 9/2008 | |
| KR | 10-2009-0001349 | | 1/2009 | |
| KR | 10-2013-0002623 | | 1/2013 | |
| KR | 101643857 B1 | | 7/2016 | |
| KR | 102016120426 | | 10/2016 | |
| KR | 101738862 B1 | | 5/2017 | |

* cited by examiner

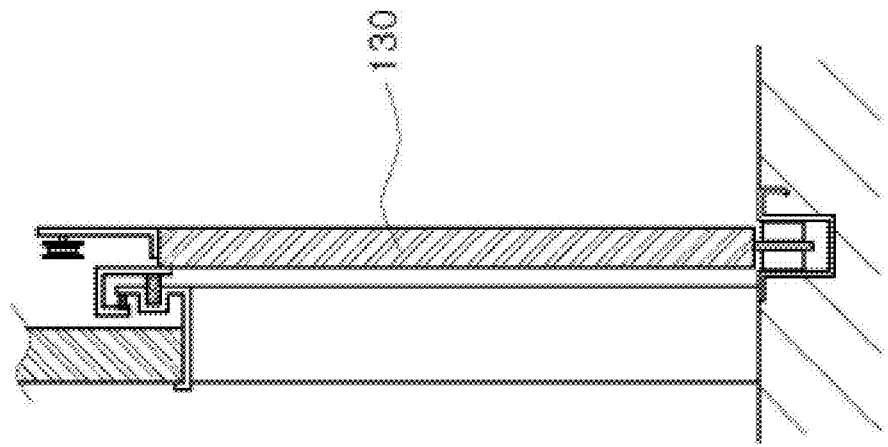
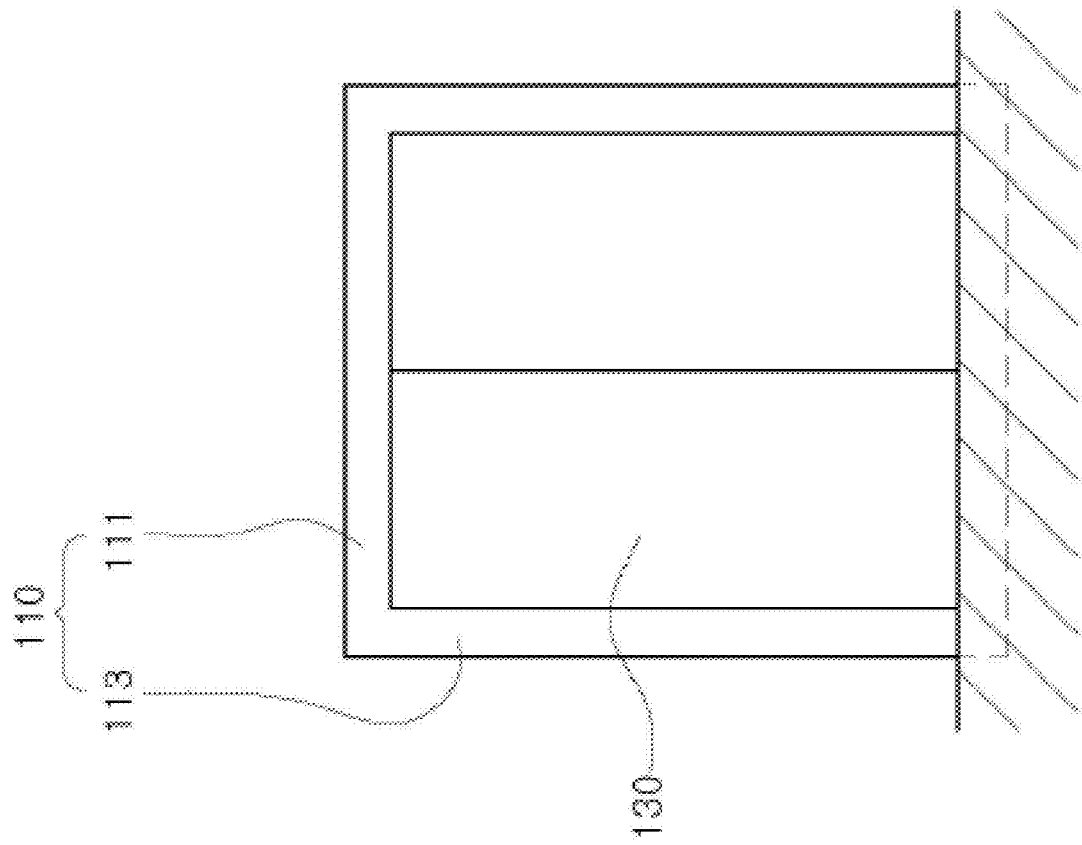
FIG. 4B
FIG. 4A

EMERGENCY ELEVATOR

TECHNICAL FIELD

The present invention relates to an emergency elevator having a cleaning function and, more particularly, to an emergency elevator capable of preventing smoke, harmful gases and flames from entering an elevator car when a fire occurs in a building, capable of enabling people on a fire-occurring floor and upper floors thereof to quickly and safely evacuate through the emergency elevator, capable of extending the life of a cage occupant in the event of an emergency using an emergency rescue device provided in the cage, capable of safely rescuing patients, expectant mothers and elderly people, and capable of removing harmful substances such as harmful gases, fine dust, germs, viruses, bacteria and the like.

BACKGROUND ART

When a fire occurs in a high-rise building, it is difficult to safely evacuate people on a fire-occurring floor and upper floors thereof due to the harmful gases, smoke and flames generated by the fire.

Since the fire occurring in such a high-rise building has a characteristic that it spreads instantaneously, it is not easy to complete the evacuation within the initial effective time.

In particular, the elderly, pregnant women and patients in medical care facilities are experiencing difficulties in evacuation, which may become a cause of damage to the people in case of fire. This is actually occurring in various cases of fire.

In case of a fire, it is possible to evacuate more quickly using an elevator. However, in case of a fire in a high-rise building, the elevator may often serve as a passage for a fire. Therefore, in most buildings, the evacuees are evacuated through emergency stairs instead of using the elevator.

Accordingly, construction law, firefighting law and elevator-related laws require the installation of fire zones and emergency stairs in case of high-rise buildings. It is also required to install a certain number of emergency elevators that can be used in the event of a fire.

However, in actual fire scenes, harmful gases, smoke and flames generated by a fire may rapidly spread to fire zones or emergency stairs, whereby the fire zones or the emergency stairs may fail to function in some cases.

In addition, it is often impossible to evacuate using emergency stairs or a rooftop due to a fire that spreads along the outer wall of a building.

Moreover, the emergency elevator according to the current standard is insufficient in the performance of blocking smoke, heat and flames and safely operating when a fire occurs. Thus, the emergency elevator is practically used only as a passageway of firefighters.

Such an emergency elevator is manufactured by enhancing the strength thereof as compared with a general elevator, so that the emergency elevator can be operated safely in an emergency situation.

However, the conventional emergency elevator is merely equipped with an emergency power supply device and a built-in battery, and has no significant difference compared with a general elevator. Furthermore, it is difficult for the conventional emergency elevator to expect complete sealing.

Accordingly, when power is not supplied from the emergency power supply device or when the capacity of the battery is exhausted, the emergency elevator does not operate and has a difficulty in blocking smoke or flames when a fire occurs.

Further, in the conventional emergency elevator, it is impossible to immediately cope with a case where a cage stops between the entrances of two floors or a case where a person in a cage cannot wait for external rescue due to an urgent emergency situation.

In view of this, an emergency exit having a size of approximately 400 mm×500 mm may be provided on the upper portion of a cage.

However, it is practically impossible for a child, a patient, a disabled person, an aged person, a pregnant woman or an injured person to escape through a small emergency exit provided on the ceiling of a cage. It is also difficult for a rescuer to rescue a person through the emergency exit.

Meanwhile, as a result of investigation of the prior art relating to the present invention, a large number of patent documents have been searched. Some of them will be described as follows.

KR 10-1738862 B1 discloses an emergency escape system for an elevator, comprising: an opening/closing unit formed on one side of a bottom surface of an elevator car and configured to open or close a part of the bottom surface of the elevator car; an emergency escape device arranged outside the bottom surface of the elevator car so as to face the opening/closing unit, installed so as to move up and down along a height direction of the elevator car, and configured to escape an elevator car occupant to the outside of the elevator car while moving up and down along the height direction of the elevator car; an emergency escape device control unit electrically connected to the emergency escape device inside the elevator car and configured to control the ascending and descending operations of the emergency escape device; and an emergency power supply unit electrically connected to the emergency escape device control unit and the emergency escape device to supply electric power for operating the emergency escape device.

KR 10-2013-0002623 A discloses a clean room elevator, comprising: an inner main body configured to define an internal space and including a front door installed so as to be openable and closable, a rear plate provided so as to face the front door, left and right plates provided respectively on the left and right sides, a ceiling plate provided in an upper portion and a foot plate provided in a lower portion; left and right air flow path forming plates spaced apart from the left and right plates to define left and right air flow paths; a top plate spaced upward from the ceiling plate and configured to define an upper space for bringing the left and right air flow paths into communication with an upper region of the internal space formed in the inner main body; a bottom plate provided to support the foot plate on a lower side in a spaced-apart state and configured to define a lower space for bringing the left and right air flow paths into communication with a lower region of the internal space formed in the inner main body; left and right first filters respectively installed in a communication path between the lower space and the left and right air flow paths and configured to filter an incoming air; left and right second filters provided in the upper space and respectively installed in a communication path between the left and right air flow paths and the internal space to filter an incoming air; and left and right air blowers respectively disposed on left and right sides of the upper space and configured to allow an incoming air to sequentially and forcibly circulate through the internal space, the lower space, the left and right air flow paths and the upper space, wherein a large amount of air can be circulated by separately forming the air circulation flow paths on the left and right sides, and the dust collection efficiency can be increased by providing the first and second filters.

KR 10-2009-0001349 A discloses an emergency elevator, comprising: a platform door installed in an elevator platform of each floor; and an elevator car vertically movably so as to be able to stop in the elevator platform of each floor. The platform door includes a door frame installed in a platform doorway of the elevator platform, and a door installed in the door frame so as to open and close the platform doorway. The emergency elevator includes: a fire detection means for detecting a fire occurring in each floor; a control unit for outputting a control signal when a fire detection signal is inputted from the fire detection means; a gap sealing member for sealing a gap formed between the door rim and the door frame while being operated in response to the control signal of the control unit. Thus, the emergency elevator can safely evacuate elevator passengers by efficiently blocking smoke, toxic gases and flames entering into the elevator when a fire occurs.

SUMMARY OF THE INVENTION

In view of the aforementioned problems inherent in the related art, it is an object of the present invention to provide an emergency elevator capable of rapidly rescuing a patient aboard the emergency elevator and capable of protecting a passenger from harmful gases by keeping the inside of an elevator car in a clean environment.

Another object of the present invention is to provide an emergency elevator capable of quickly removing flames introduced into an elevator car to prevent a passenger from getting burned and capable of enabling a rescuer to perform emergency cleaning and emergency treatment inside an elevator car.

A further object of the present invention is to provide an emergency elevator capable of sterilizing various harmful substances introduced into an elevator car.

A still further object of the present invention is to provide an emergency elevator capable of forming an air curtain by a jet injection system when a passenger is aboard an elevator car and capable of preventing smoke and flames from entering the interior of an elevator car and removing contaminants in advance.

A yet still further object of the present invention is to provide an emergency elevator capable of preventing noxious gases, heat, smoke and flames from flowing into an elevator car by forming a refractory door and a platform door installed at a platform entrance into a completely sealed structure.

An even yet still further object of the present invention is to provide an emergency elevator capable of being safely operated by installing a packing having smoke-blocking, flame-blocking and heat-shielding performance in a refractory door and a platform door.

An additional even yet still further object of the present invention is to provide an emergency elevator capable of enabling a passenger to safely escape to a safety zone when an abnormality occurs in the emergency elevator and an elevator car does not move.

An additional even yet still further object of the present invention is to provide an emergency elevator capable of being operated even during a normal time.

In order to achieve the above objects, there provided an emergency elevator, including: a door frame installed on upper, left and right sides of an entrance of an elevator platform provided on each floor; an elevator car configured to vertically move along an elevator passage and to stop in the elevator platform of each floor and provided with a pair of elevator doors configured to be slidingly opened and closed; a pair of platform doors installed in the door frame so as to be slidingly opened and closed in association with the elevator doors; a lower frame installed on a lower side of the entrance of the elevator platform and configured to slidably support the platform doors; an upper door rim installed on an upper side of the platform doors; a side door rim vertically installed at a lateral end of the platform doors; an oxygen supply device configured to supply oxygen to a patient in the elevator car, the oxygen supply device including an oxygen generator unit disposed at an upper portion of the elevator car, an oxygen storage container configured to store oxygen, a length-adjustable oxygen mask unit disposed inside the elevator car and connected to the oxygen storage container so as to supply oxygen to the patient; an emergency ventilation device configured to supply a purified air into the elevator car and to discharge a contaminated air, the emergency ventilation device including an air purifying device installed at the upper portion of the elevator car, a blowing duct configured to connect the air purifying device to a blowing hole formed in an upper plate of the elevator car and to supply the purified air into the elevator car, an air intake duct configured to connect the air purifying device to an air intake hole formed at a side lower end of the elevator car and to draw the contaminated air in the elevator car to supply the contaminated air to the air purifying device, and a sterilizing/disinfecting device provided on one side of the air purifying device and configured to remove and sterilize noxious substances in an air; and a filter device provided in the blowing duct so as to remove harmful substances introduced into the elevator car, wherein the platform doors are configured to make contact with a middle portion of the upper door rim at an inner end thereof and coupled to the upper door rim in a zigzag shape, an upper sealing part is formed between the upper door frame and the upper door rim, a side sealing part is formed between the side door frame and the side door rim, a lower sealing part is formed between each of the platform doors and the lower frame, and each of the upper sealing part, the side sealing part and the lower sealing part includes a sealing member.

The emergency elevator may further include: a lighting device provided outside the elevator car so as to enable a person to safely escape from the elevator car and to be operated by a self-charged emergency power supply system; and an emergency escape device configured to enable a person to escape when the elevator car is stopped, wherein the emergency escape device includes an upper hatch openably installed at the upper portion of the elevator car so as to enable a person to escape to an upper side of the elevator car, a lower hatch openably installed at a bottom of the elevator car so as to enable a person to escape to a lower side of the elevator car, a slow descent device installed on a horizontal member connecting a pair of vertical car frames, and a safety bar foldably installed inside the elevator car so as to enable a person to grip the safety bar when escaping to the lower side of the elevator car.

The emergency elevator may further include: an emergency medical instrument and a first-aid kit provided inside the elevator car and removably stored in an inner wall of the elevator car.

The emergency elevator may further include: a sprinkler installed at the upper portion of the elevator car; and a cleaning device removably stored in the inner wall of the elevator car so as to supply water stored in a water tank.

In the emergency elevator, the filter device provided in the blowing duct may include a HEPA filter and an ULPA filter.

The emergency elevator may further include: an ultraviolet lamp configured to irradiate ultraviolet rays to an air passing through the blowing hole.

In the emergency elevator, the filter device may include an activated charcoal filter.

In the emergency elevator, the filter device may include a silver nano filter.

The emergency elevator may further include: a jet injection system installed above the elevator doors so as to form an air curtain in a platform doorway where the elevator car is stopped.

In the emergency elevator, the air intake hole is closed and air amount blowing from the blowing hole is increased when elevator car is stopped on a fire-occurring floor and elevator door is opened.

The emergency elevator may further include: a sealing member provided on each of coupling surfaces of the platform doors.

In the emergency elevator, the upper sealing part may be configured so that a sealing member is inserted into a transverse accommodation portion formed in the upper door rim so as to make close contact with the upper door frame, and so that a sealing member is inserted into an insertion groove formed in the upper door frame so as to make close contact with an inner surface of each of the platform doors.

In the emergency elevator, the side sealing part may be configured so that a sealing member is inserted into a vertical accommodation portion formed in the side door rim so as to make close contact with the side door frame, and so that a sealing member is inserted into an insertion groove formed in the side door frame so as to make close contact with an outer surface of each of the platform doors.

In the emergency elevator, the lower sealing part may be configured so that a metal shielding plate is installed at a lower portion of each of the platform doors, and so that an accommodation space having a predetermined width is formed in the lower frame to accommodate a sealing member attached to each side surface of the metal shielding plate.

In the emergency elevator, the sealing member may include a graphite bar and a graphite plate.

The emergency elevator may further include: a fire detection unit configured to detect a fire occurring on each floor; and a refractory door rotatably installed in a platform doorway and configured to close the platform doorway in response to a signal transmitted from the fire detection unit.

In the emergency elevator, the refractory door may include a pair of rotary doors rotatably installed on side walls of the platform doorway and configured to engage with each other in a zigzag shape to close the platform doorway.

In the emergency elevator, the refractory door may include a sliding door configured to be slidably opened and closed so that, when closed, the sliding door is accommodated inside a wall defining the platform doorway.

The emergency elevator may further include: a gap sealing member provided at a lower portion of each of the platform doors, wherein the gap sealing member includes a metal shielding plate installed at the lower portion of each of the platform doors along a longitudinal direction, a lower door rim installed at the lower portion of each of the platform doors and provided with an entrance portion through which the metal shielding plate passes and an accommodation space having a predetermined size, a heat-resistant packing installed in the accommodation space and configured to make contact with a lower portion of the metal shielding plate at an upper end thereof, and a door guide shoe installed in the metal shielding plate so as to make contact with the entrance portion of the lower door rim and configured to guide movement of the platform doors.

In the emergency elevator, switches for operating the refractory doors may be installed on an inner side of the platform doorway and on an elevator outer wall, and each of the switches may be configured to independently operate the refractory doors.

According to the present invention, in an emergency situation such as a fire or the like, oxygen or a purified air is supplied to the inside of an elevator car to enable a passenger in the elevator car to breathe smoothly.

In addition, by virtue of an oxygen supply device and an emergency ventilation device, oxygen is supplied to a passenger to suffocation accident, and a purified air is supplied while discharging a contaminated air in an elevator car, thereby enabling a passenger in the elevator car to breathe smoothly.

Furthermore, since an emergency medical instrument, a first-aid kit and a cleaning device are provided in the elevator car, it is possible to protect various types of patients and injured persons and to immediately cope with an emergency situation.

Moreover, since a sprinkler is installed at the upper portion of the elevator car, it is possible to quickly remove the flames spreading into the elevator car and to reduce damage to a passenger.

In addition, various bacteria and harmful substances existing in the air inside an elevator car can be removed.

Furthermore, when a fire occurs, it is possible to prevent flames, smoke, noxious gases and the like from entering a gap between a platform door and a door frame or a gap between a platform door and a lower frame.

Moreover, when an elevator car is stopped on a fire-occurring floor and elevator door is opened, it is possible to prevent flames, smoke, noxious gases and the like from entering into an elevator car.

In addition, since an elevator car can safely pass through an evacuated fire-occurring floor, it is possible to effectively rescue a large number of passengers.

Further, since sealing is doubly performed by an upper sealing portion and a side sealing portion between a platform door and a door frame, it is possible to completely seal the gap between the platform door and the door frame when the platform door is closed.

In addition, since sealing members are attached to both sides of a metal shield plate provided at the lower portion of a platform door, and are brought into close contact with the inner surface of a lower frame to provide double seals. Thus, it is possible to completely seal a gas between a platform door and a lower frame when the platform door is closed.

Further, a refractory door provided at the end portion of a platform doorway can prevent flames, smoke, noxious gases and the like generated by a fire from entering the platform doorway.

Further, since gap sealing members made of a heat-resistant packing are provided between a platform door and a door frame and at the lower portion of the platform door, it is possible to prevent smoke or noxious gases from flowing into an elevator passage even when smoke or noxious gases is introduced into a platform doorway due to the occurrence of an abnormality in a refractory door.

Further, since an emergency escape device is provided, when an elevator car is stopped between floors, it is possible for a passenger to escape by using an upper hatch and a slow descent device.

Moreover, a child, an elderly person and a patient who has a difficulty in using an upper hatch can escape from an elevator car through a lower hatch.

In addition, as since a lighting device is provided in an elevator car, it is possible for a passenger escaping from the elevator car to safely evacuate. It is also possible for a rescuer to quickly move and transport an injured person.

In addition, the emergency elevator may be operated and used even during a normal time at which a fire does not occur.

BRIEF DESCRIPTION OF THE DRAWINGS

FIGS. 4A and 4B are a schematic front view and a schematic sectional side view for explaining a door sealing device according to the first embodiment of the present invention.

MODE FOR CARRYING OUT THE INVENTION

Preferred embodiments of an emergency elevator according to the present invention will now be described in detail with reference to the accompanying drawings.

First Embodiment

FIGS. 1 to 8 show an emergency elevator according to a first embodiment of the present invention.

Figure 1:
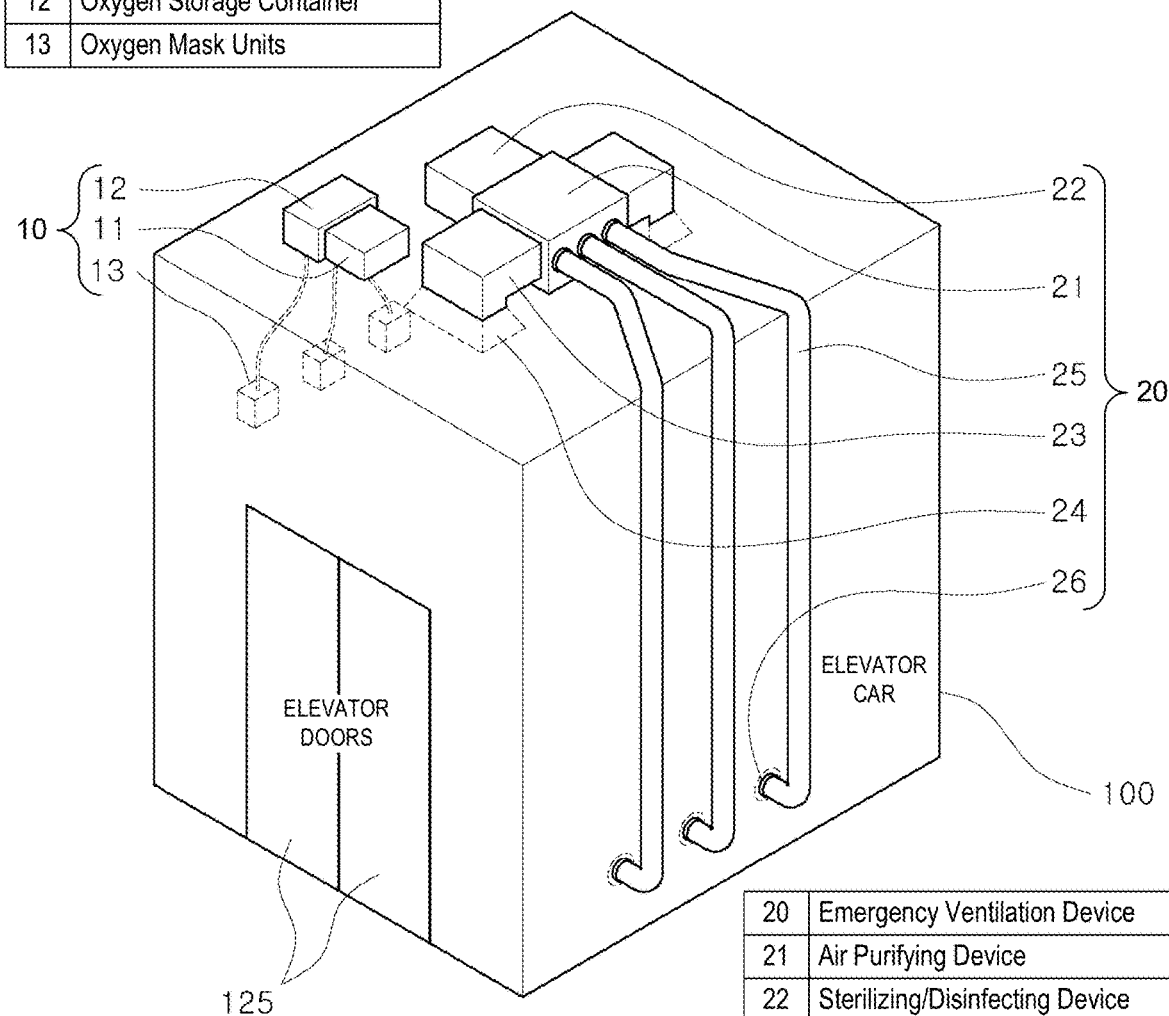
FIG. 1 is a schematic view for explaining the concept of an emergency elevator according to a first embodiment of the present invention.
Figure 2:
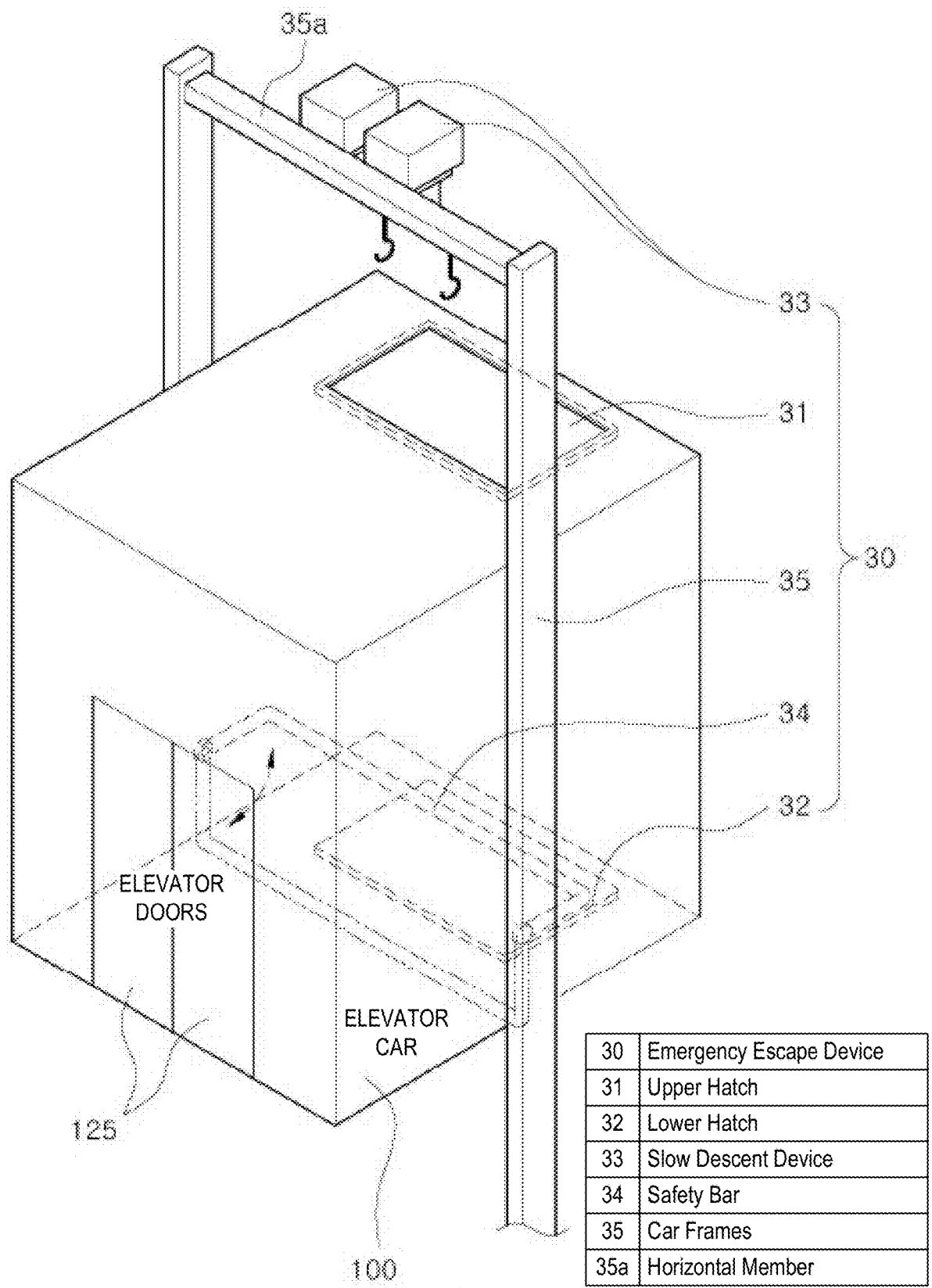
FIG. 2 is a schematic view showing an emergency escape device according to the first embodiment of the present invention.

As shown in FIGS. 1 and 2, the emergency elevator according to the first embodiment of the present invention includes: an oxygen supply device 10 configured to supply oxygen to a patient inside an elevator car 100; an emergency ventilation device 20 configured to supply a purified air into the elevator car 100 and to discharge a contaminated air; and an emergency escape device 30 used for emergency escape when the elevator car 100 is stopped.

The oxygen supply device 10 includes an oxygen generator unit 11 disposed at an upper portion of the elevator car 100, an oxygen storage container 12 configured to store oxygen, and a length-adjustable oxygen mask unit 13 disposed inside the elevator car 100 and connected to the oxygen storage container 12 so as to supply oxygen to a patient.

The oxygen mask unit 13 is preferably accommodated in a storage space closed by a lid (not shown) during a normal time. If necessary, the lid is opened to pull out the oxygen mask unit 13.

Accordingly, when a person aboard the elevator car 100 has a difficulty in breathing, oxygen is supplied to the person through the oxygen mask unit 13, thereby preventing suffocation due to the lack of oxygen.

The emergency ventilation device 20 includes an air purifying device 21 installed at an upper portion of the elevator car 100, a blowing duct 23 installed to connect a blowing hole 24 penetrating a top plate of the elevator car 100 to the air purifying device 21 and configured to supply a purified air to the upper inner side of the elevator car 100, an air intake duct 25 installed to connect an air intake hole 26 penetrating the lower end of a side surface of the elevator car 100 to the air purifying device 21 and configured to draw a contaminated air in the elevator car 100 and supply the contaminated air to the air purifying device 21, and a sterilizing/disinfecting device 22 installed on one side of the air purifying device 21 to remove and sterilize toxic substances in the air.

When smoke or a noxious gas enters the elevator car 100 so that the normal breathing is difficult, the air purifying device 21 is operated to draw the smoke and the noxious gas in the elevator car 100. Then, the sterilization and disinfection are performed by the sterilizing/disinfecting device 22 to purify an air. The purified air is supplied into the elevator car 100 through the blowing hole 24. Thus, the persons aboard the elevator car 100 can normally breathe using the purified air.

Also, the air intake hole 24 is closed and air amount blowing from the blowing hole 26 is increased when elevator car 100 is stopped on a fire-occurring floor and elevator door is opened.

Thus, it is possible to prevent flames, smoke, noxious gases and the like from entering into an inside of the elevator car 100 from the outside.

The emergency escape device 30 includes an upper hatch 31 openably provided at the upper portion of the elevator car 100 so as to enable a person to escape to the upper side of the elevator car 100, a lower hatch 32 openably provided on the bottom of the elevator car 100 so as to enable a person to escape to the lower side of the elevator car 100, a slow descent device 33 installed at an upper portion of the elevator car 100 so that the person escaped to the upper side of the elevator car 100 can go down using the slow descent device 33, and a safety bar 34 foldably installed at a lower portion of the elevator car 100 so that the person escaped to the lower side of the elevator car 100 can hold the safety bar 34.

As shown in FIG. 2, the slow descent device 33 is installed on a horizontal member 35a connecting the upper portions of a pair of car frames 35.

According to the above-described structure, when the elevator car 100 is stopped and does not move, a person may open the upper hatch 31 to escape to the upper side of the elevator car 100 and then may safely move down using the slow descent device 33.

A person who cannot use the upper hatch 31, such as a child, an elderly person or a patient, may open the lower hatch 32 to escape to the lower side of the elevator car 100.

At this time, by unfolding the safety bar 34, the person may safely escape while holding the safety bar 34.

Although not shown in the drawings, each of the upper and lower hatches 31 and 32 are configured to be hermetically sealed by a sealing member at a normal time.

Figure 3:
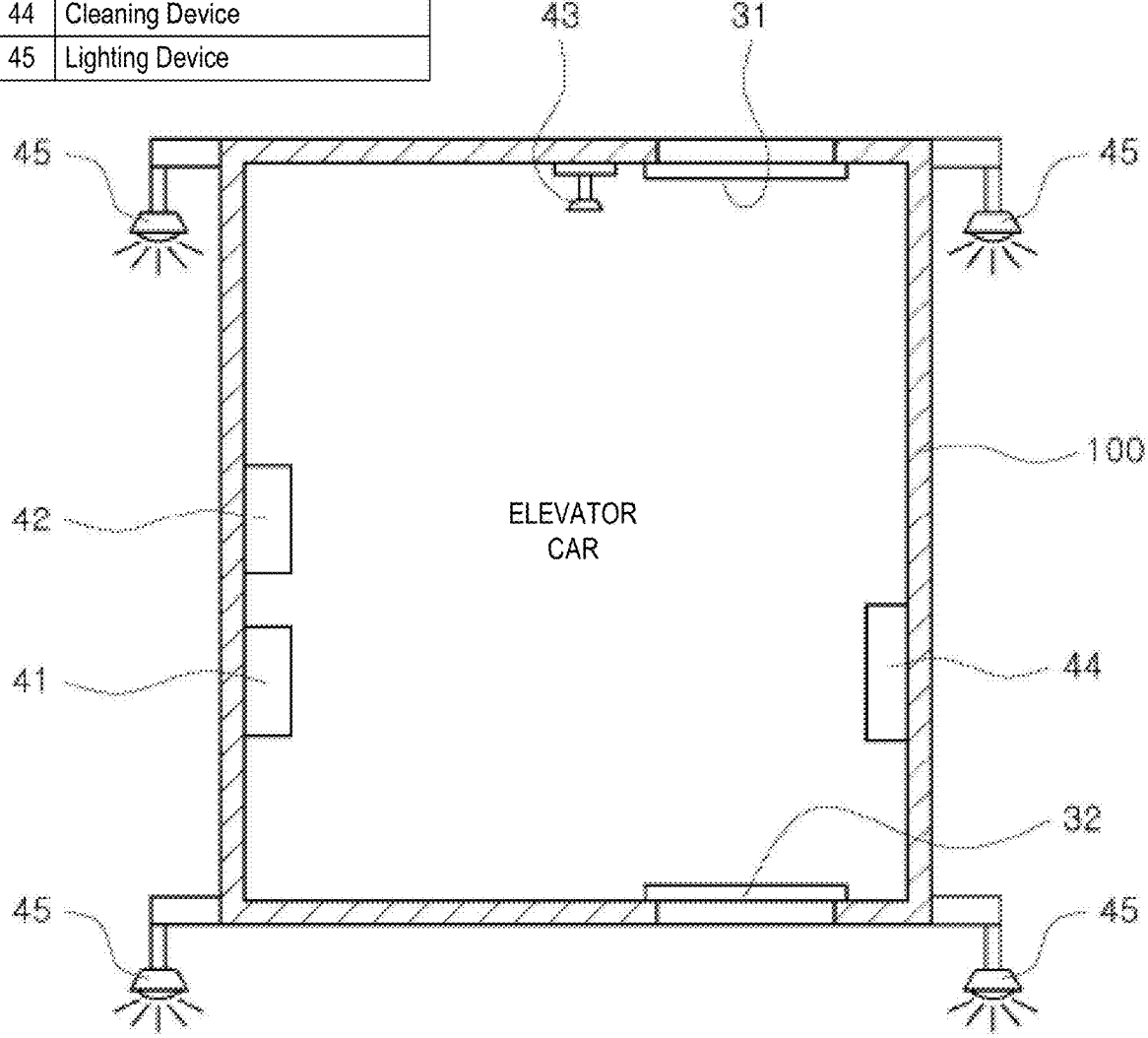
FIG. 3 is a schematic sectional view showing the inside of the emergency elevator according to the first embodiment of the present invention.

As shown in FIG. 3, a lighting device 45 operated by a self-rechargeable emergency power supply system is installed at the top and bottom of the elevator car 100 so that the person escaping from the elevator car 100 can safely move.

Accordingly, the person escaping through the use of the slow descent device 33 or the person escaping through the lower hatch 32 may move quickly without wandering in the dark, and the rescuer may quickly move to protect the escaping person.

In addition to the oxygen supply device 10, the emergency ventilation device 20 and the emergency escape device 30, there may be further provided devices used for various accidents occurring in the interior of the elevator car 100.

That is to say, as shown in FIG. 3, an emergency medical instrument 41 and a first-aid kit 42 may be further provided in the interior of the elevator car 100.

Accordingly, when an abnormality occurs in the heart of an injured person or a patient, the emergency medical instrument 41 may be used to cope with such a situation, and the injured person may be treated with the first-aid kit 42.

The emergency medical instrument 41 and the first-aid kit 42 are preferably provided so as to be accommodated in the inner wall of the elevator car 100.

This is to maximize the internal space of the elevator car 100 and to facilitate the escape of a person from the elevator car 100.

As shown in FIG. 3, a sprinkler 43 is further provided on the upper side of the elevator car 100. In this case, all of the electric devices and electronic devices in the elevator car 100 are provided in a waterproof manner so that they are not affected by the operation of the sprinkler 43.

The sprinkler 43 can prevent flames from spreading into the interior of the elevator car 100 and can minimize the damage which may be caused by the flames.

A cleaning device 44 for providing water stored in a water tank is preferably installed in the inner wall of the elevator car 100 so as to urgently clean the eyes or the affected part of a patient exposed to flames or a noxious gas.

In addition to the above-described emergency exit devices, the emergency elevator further includes a filter device (not shown) provided in the air blowing duct 23 to remove harmful substances such as bacteria, fine dust or the like to maintain a clean state.

The filter device installed in the blowing duct 23 is preferably a HEPA filter or an ULPA filter.

The HEPA filter is a kind of high performance filter that removes fine particles in the air and refers to a high efficiency particulate air filter.

According to the criteria of the American Atomic Energy Commission, it is recognized as a HEPA filter if 99.97% of particles larger than 0.3 µm can be removed.

The HEPA filter has been developed to remove radioactive particles in the air and is usually produced by compressing glass fibers. The HEPA filter has a structure similar to a net and ensures that particles cannot pass therethrough.

The ULPA (Ultra Low Penetration Air) filter is a high-efficiency filter that can filter 99.999% or more of ultrafine particles of 100 nm in size.

The ULPA filter is superior to the glass fiber filter in differential pressure and filtration performance and is used as a filter for air conditioning in semiconductor, electronics, biotechnology facilities and the like.

Furthermore, the emergency elevator further includes an ultraviolet lamp (not shown) for irradiating ultraviolet rays to the air passing through the blowing hole 24 so as to kill germs, bacteria and viruses introduced into the interior of the elevator car 100.

The filter device may further include an activated charcoal filter or a silver nano filter.

The activated charcoal filter adsorbs and removes odorous substances, and the silver nano filter improves the sterilizing effect.

Since the ultraviolet lamp, the activated charcoal filter and the silver nano filter are well known in the art, a detailed description thereof will be omitted.

Further, a jet injection system (not shown) is provided above the elevator door 125 so that an air curtain is formed in front of the elevator door of the platform doorway where the elevator car 100 stops.

The jet injection system can suppress the introduction of smoke and contaminants from the outside.

As shown in FIGS. 4 to 8, the emergency elevator further includes a door sealing device for sealing the door of the elevator.

Hereinafter, the door sealing device according to a first embodiment of the present invention will be described in detail.

As shown in FIGS. 4A and 4B, a door frame 110 is provided on the upper side and lateral sides of the elevator car 100. The door frame 110 includes an upper door frame 111 and a pair of side door frames 113

Figure 5A:
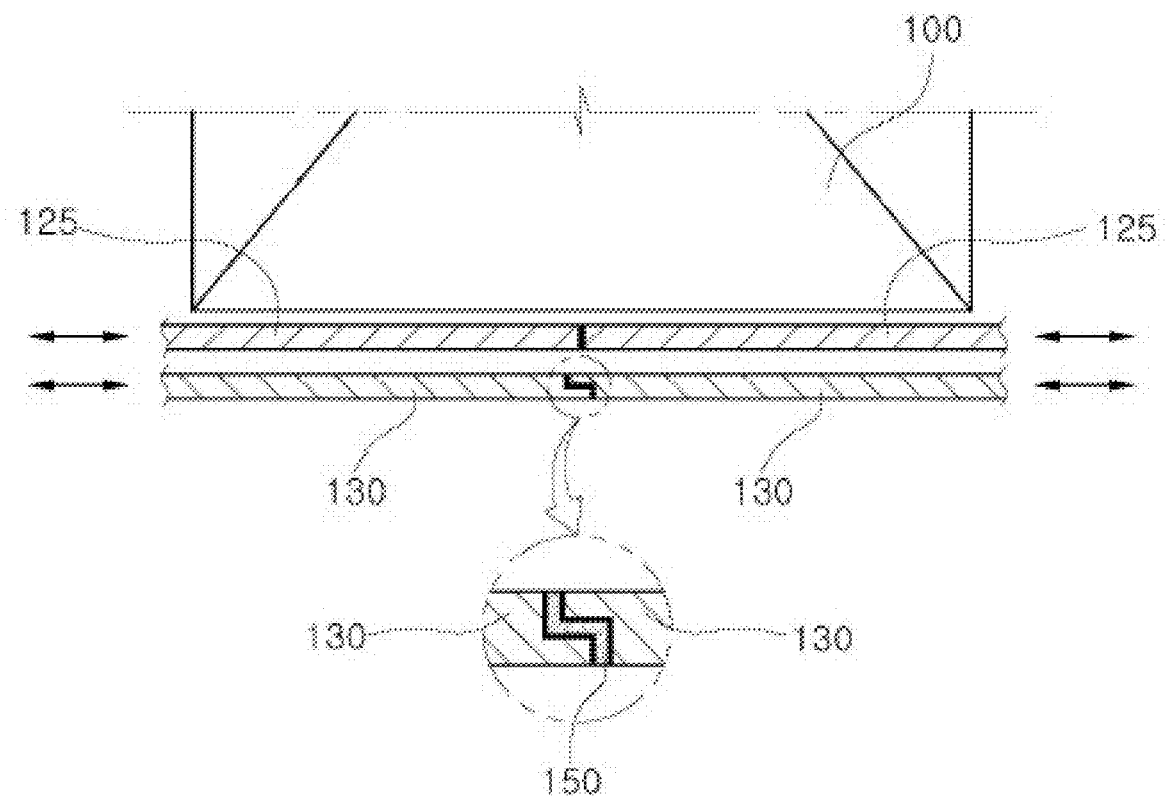
FIGS. 5A and 5B are plan views showing different examples of a contact portion of a platform door according to the first embodiment of the present invention.
Figure 5B:
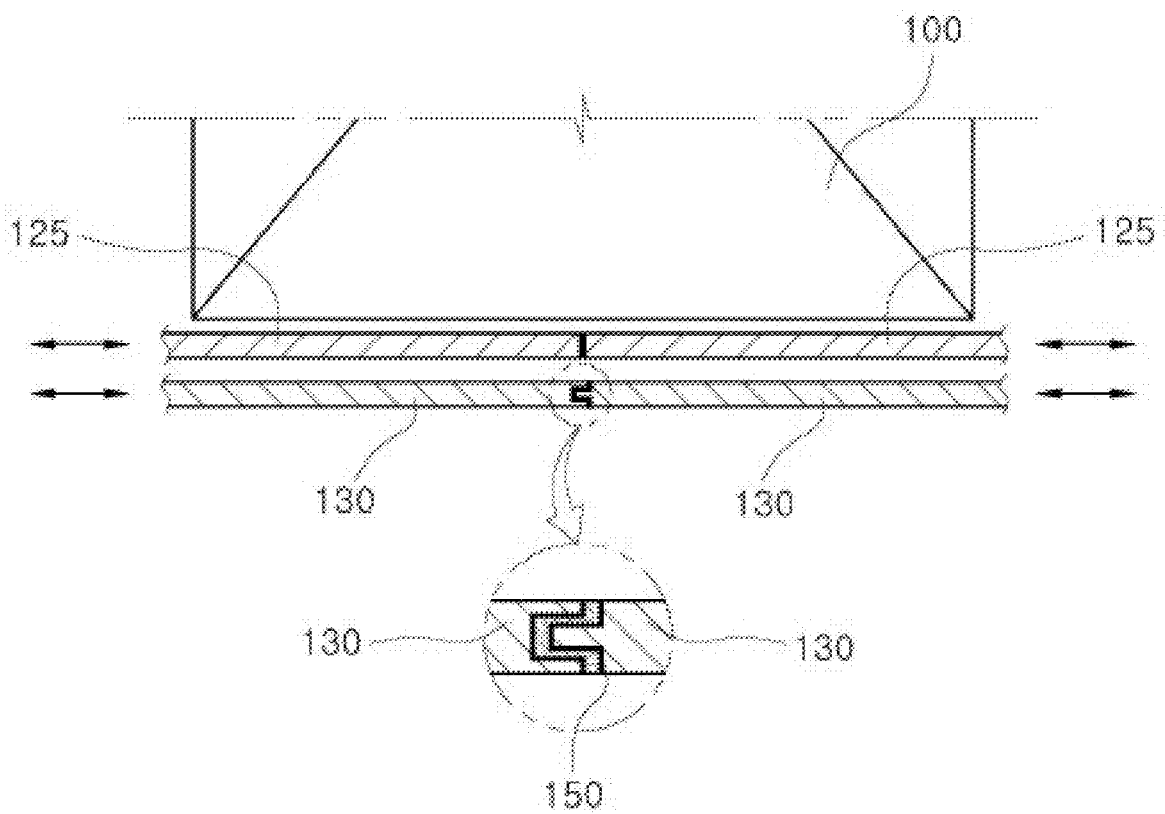

As shown in FIGS. 5A and 5B, the inner ends of a pair of platform doors 130 abut against the upper door frame 111 at an intermediate position of the upper door frame 111 and are coupled to the upper door frame 111 in a staggered or concavo-convex shape.

Figure 6:
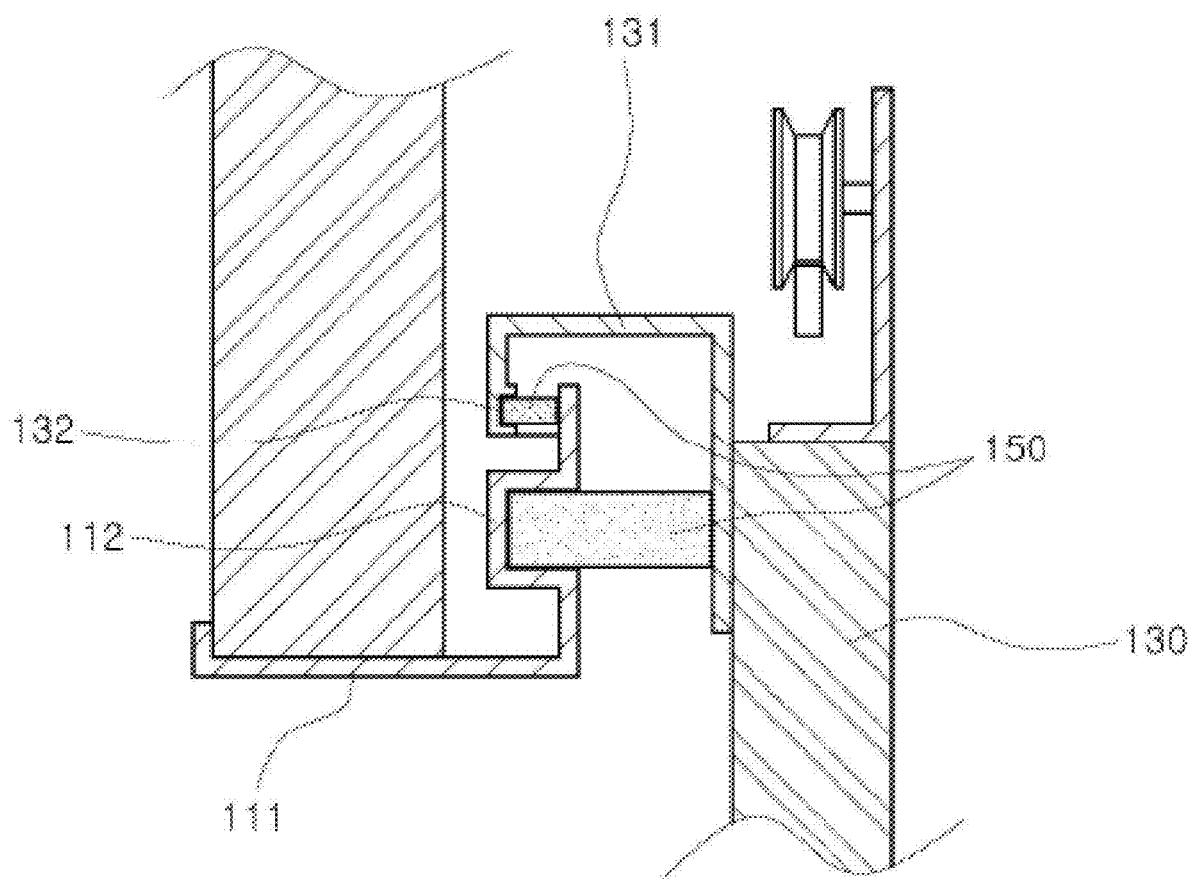
FIG. 6 is a sectional side view of an upper sealing part according to the first embodiment of the present invention.
Figure 7:
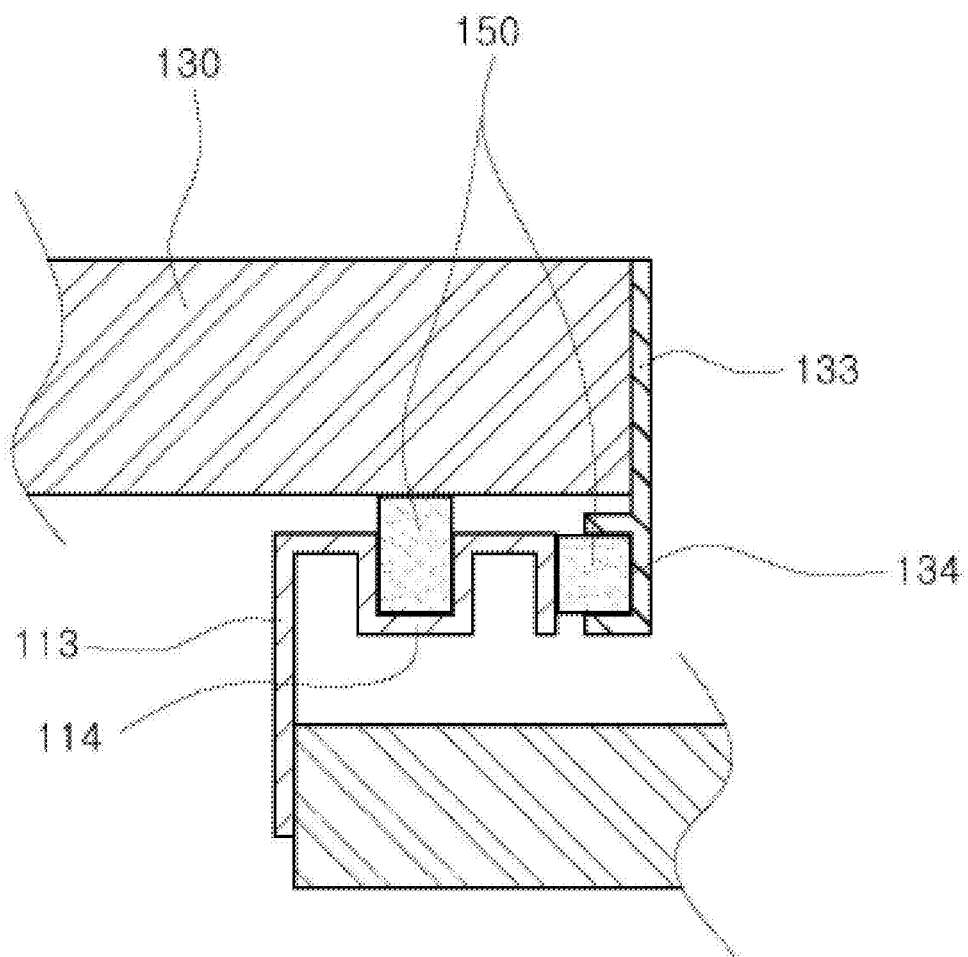
FIG. 7 is a sectional plan view of a side sealing part according to the first embodiment of the present invention.
Figure 8:
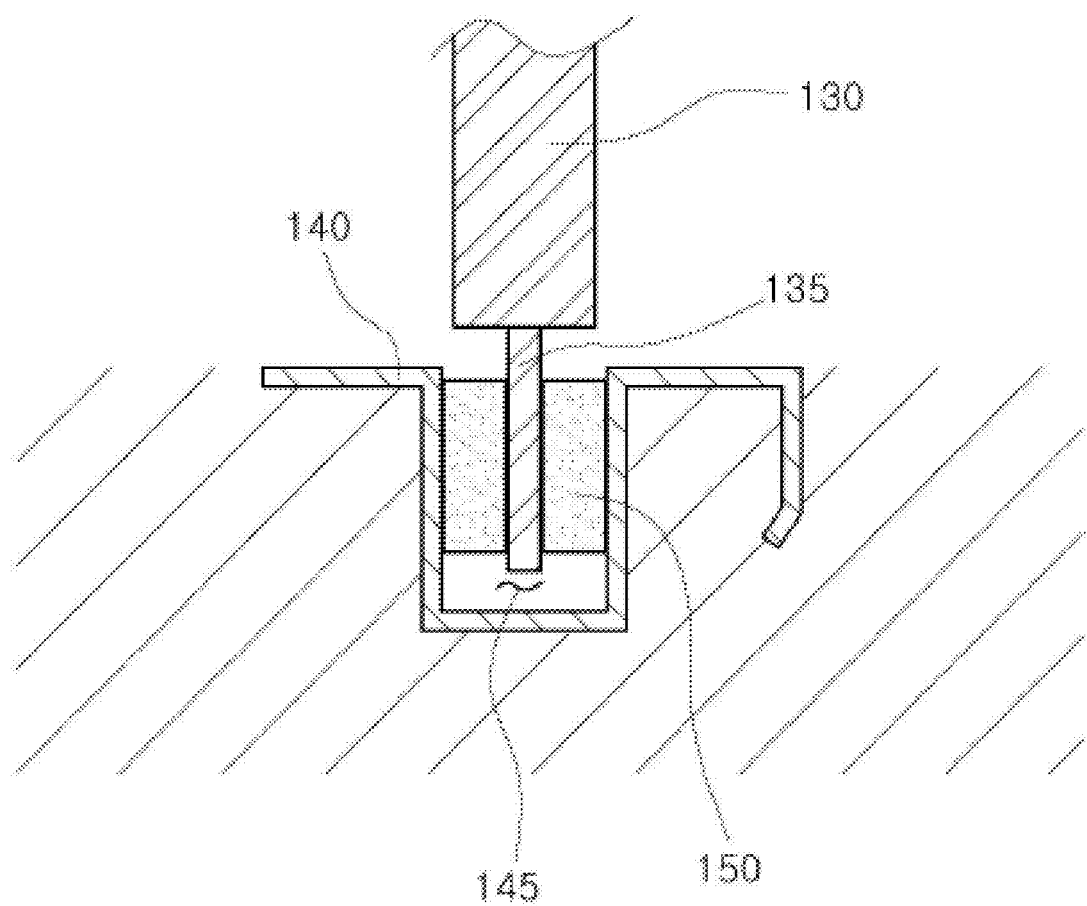
FIG. 8 is a sectional side view of a lower sealing part according to the first embodiment of the present invention.
Figure 9:
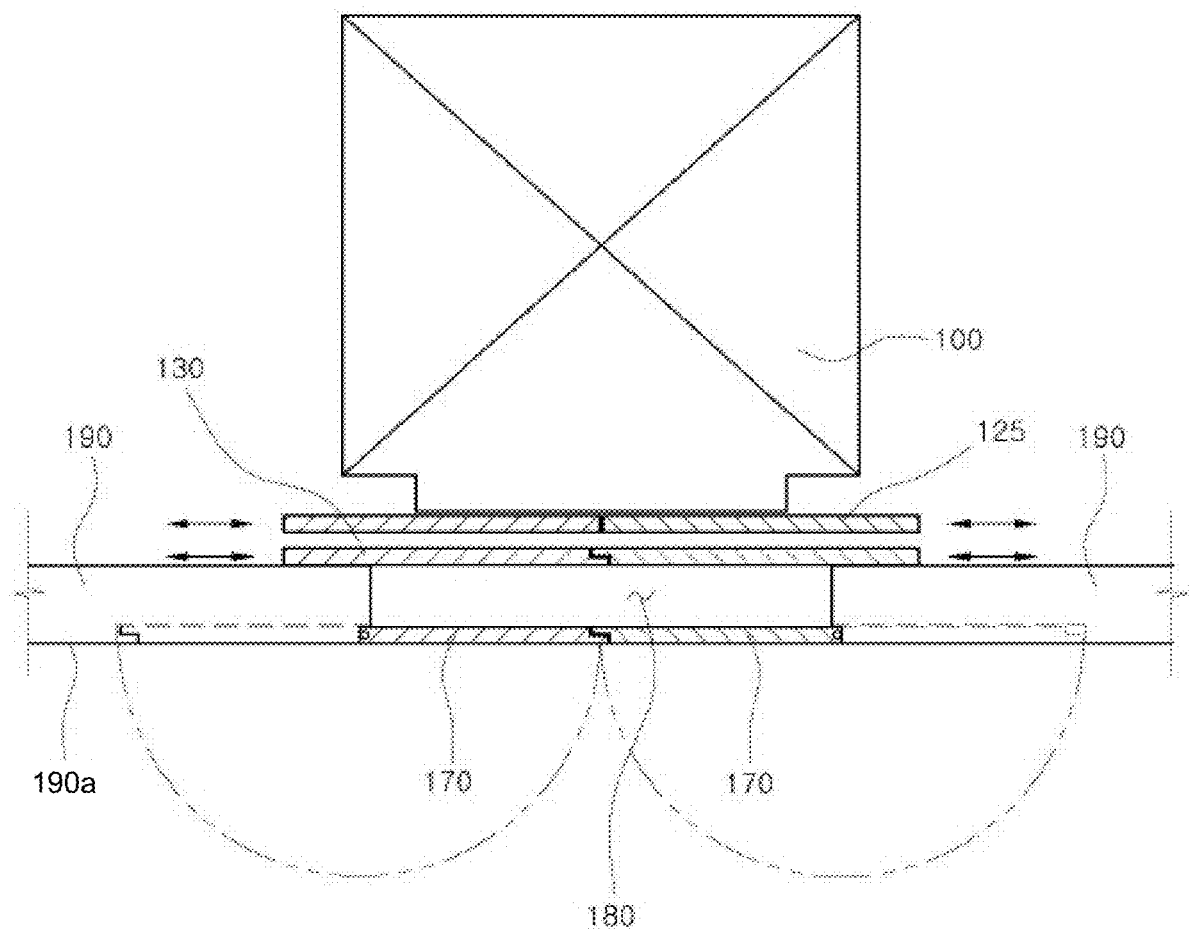
FIG. 9 is a plan view of an emergency elevator according to a second embodiment of the present invention.
Figure 10:
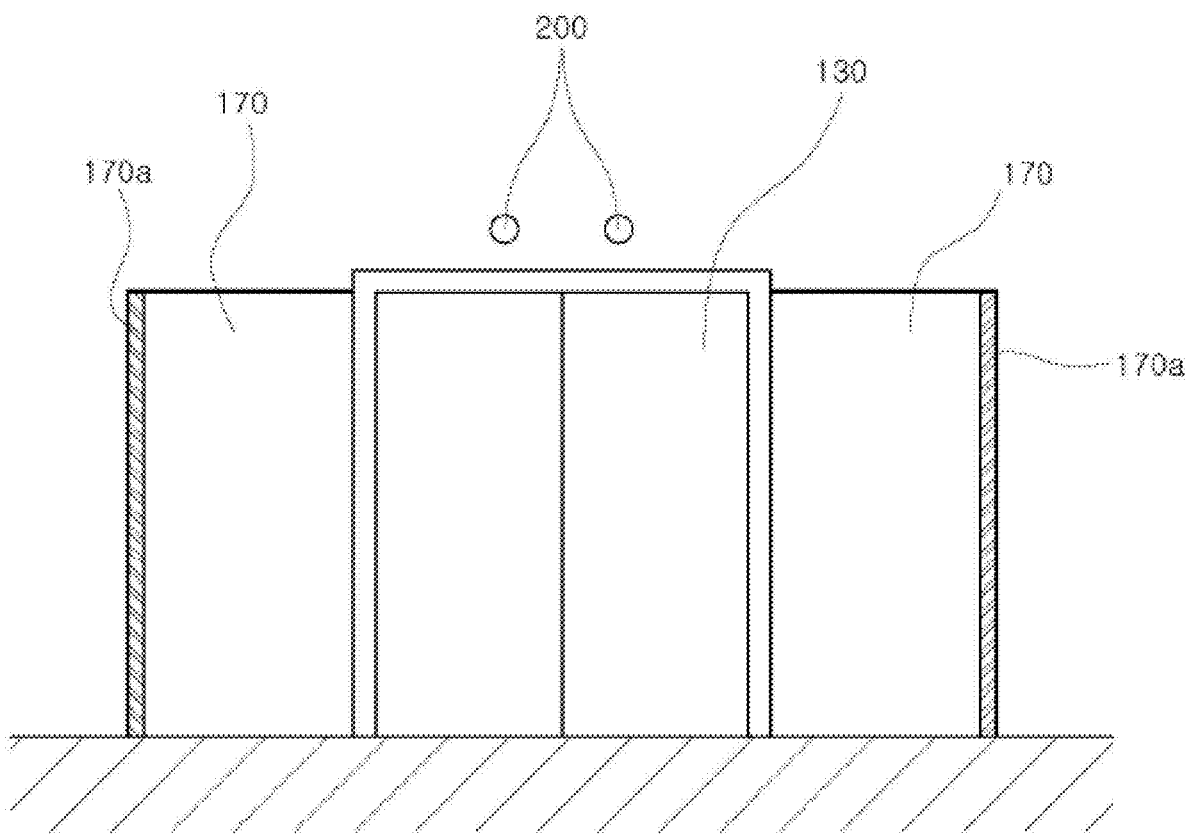
FIG. 10 is a front view of the emergency elevator according to the second embodiment of the present invention.
Figure 11:
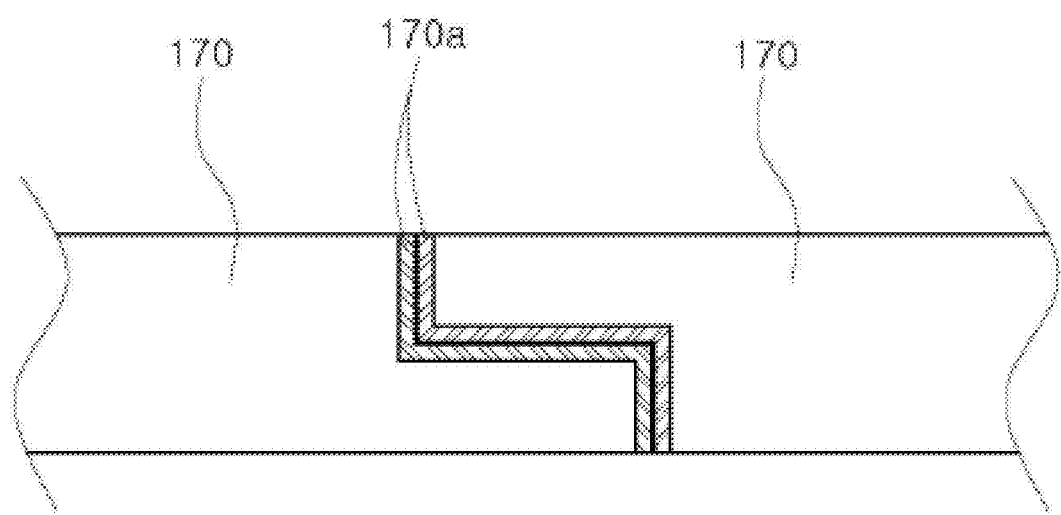
FIG. 11 is a sectional plan view of a refractory door according to the second embodiment of the present invention.

As shown in FIG. 6, an upper sealing part is formed between the upper door frame 111 and the upper door rim 131. As shown in FIG. 7, a side sealing part is formed between each of the side door frames 113 and each of the side door rims 133. As shown in FIG. 8, a lower sealing part is formed between the platform doors 130 and the lower frame 140.

Each of the sealing parts is sealed by at least one sealing member 150. The sealing member 150 may be attached to the coupling surface of the elevator car 100.

With the above structure, when the platform doors 130 is closed, a gap is sealed by the sealing member 150 so that flames, heat, smoke and the like are not introduced into the platform doorway.

As shown in FIG. 6, in the upper sealing part, a sealing member 150 is inserted into a transverse accommodation portion 132 formed in the upper door rim 131 bent twice so that the end portion thereof is positioned inside the upper door frame 111. Thus, the sealing member 150 makes close contact with the upper door frame 111. Another sealing member 150 is inserted into a transverse insertion groove 112 of the upper door frame 111 so as to be in close contact with the upper door frame 111. Thus, the sealing member 150 makes close contact with the inner surface of the platform doors 130.

In order to allow the sealing member 150 in the insertion groove 112 to come into close contact with the inner surface of the platform doors 130, the upper end of the platform doors 130 needs to be positioned higher than the lower end of the upper door frame 111 by 100 mm Or more.

However, if the height of the platform doors 130 is too high, the manufacturing cost will increase. Therefore, the upper limit of the height difference is preferably 150 mm.

According to the above structure, when the platform doors 130 is closed, the upper door frame 111, the platform doors 130 and the upper door rim 131 are double-sealed by the two sealing members 150.

As a result, is possible to prevent flames, heat, and smoke generated in the fire scene from entering the elevator car 100.

As shown in FIG. 7, in the side sealing part, a sealing member 150 is inserted into a vertical accommodation portion 134 formed at the end portion of a side door rim 133 protruding forward, so that the sealing member 150 makes close contact with the end surface of the side door frame 113. Another sealing member 150 is inserted into a vertical insertion groove 114 formed in the side door frame 113, so that the sealing member 150 makes close contact with the outer surface of the platform doors 130.

With the above structure, when the platform doors 130 is closed, the side door frame 113, the platform doors 130 and the side door rim 133 are double-sealed by the two sealing members 150.

As shown in FIG. 8, in the lower sealing part, a transverse metal shielding plate 135 is installed in the lower portion of the platform doors 130. An accommodation space 145 having a predetermined width is formed in the lower frame 140 so as to accommodate sealing members 150 that make close contact with the side surfaces of the metal shielding plate 135.

That is, the sealing members 150 attached to both sides of the metal shielding plate 135 make close contact with the side surfaces defining the accommodation space 145 of the lower frame 140, so that double sealing is made when the platform doors 130 is closed.

Therefore, it is possible to prevent flames, heat, smoke and the like from being introduced into the elevator car 100 through a gap between the platform doors 130 and the lower frame 140.

A graphite bar or a graphite plate may be used as the sealing member 150. It is preferable that a graphite bar is used as the sealing member in the upper sealing part or the side sealing part, and a graphite plate is used as the sealing member in the lower sealing part.

The sealing member attached to the contact surface of the platform doors 130 is preferably formed of a heat-resistant packing.

According to the emergency elevator of the first embodiment of the present invention, it is possible to prevent flames, smoke, noxious gases and heat from entering the elevator passageway when a fire occurs. This makes it possible to evacuate quickly using the emergency elevator.

In addition, when there is a possibility that flames or smoke may be introduced into the elevator passageway from the fire-occurring floor or the completely evacuated floor, the elevator car 100 is not stopped on the fire-occurring floor or the completely evacuated floor, and the platform doors 130 is not opened on the fire-occurring floor or the completely evacuated floor. This makes it possible to prevent flames, smoke and harmful gases from entering the elevator passage.

When the platform doors 130 is closed, flames, smoke and harmful gases are double-blocked by the platform doors 130, the upper sealing part positioned above the platform doors 130, the side sealing parts positioned on both sides of the platform doors 130 and the lower sealing part positioned below the platform doors 130.

Therefore, the safety in the elevator passage is secured so that persons can quickly evacuate using the elevator car 100 of the emergency elevator.

Generally, the elevator passage provided in a high-rise building is a fireproof zone. However, a fireproof door may be opened by a panicked evacuee in case of a fire.

Furthermore, since a small number of fire-fighting devices are provided in most fireproof zones or emergency stairs, it is not easy for many people to evacuate quickly.

In particular, it is virtually impossible to evacuate people within one hour in a high-rise building where a fire spreads rapidly.

According to the present invention, the emergency elevator may be operated even during the occurrence of a fire. Thus, it is possible to quickly rescue people on the fire-occurring floor and the upper floors thereof, thereby reducing damage of human.

In addition, the air inside the elevator car 100 can be maintained as clean as possible by a HEPA filter, an ULPA filter, an activated charcoal filter, a silver nano filter, or an ultraviolet lamp provided in the elevator car 100.

Further, by forming an air curtain using the jet injection system provided on the upper side of the elevator door, it is possible to prevent harmful substances or contaminants from entering the elevator car 100.

In addition, the occurrence of suffocation can be prevented by the oxygen supply device and emergency ventilation device, thereby enabling people to breathe smoothly.

The emergency medical instrument, the first-aid kit and the cleaning device can also be used to provide first aid to the injured person.

Moreover, the sprinkler can remove the flames introduced into the elevator car, thereby preventing a passenger form getting burned.

In the case where the emergency elevator can no longer be operated, the emergency escape devices such as the lighting device, the slow descent device and the like can be used to allow a passenger to escape to the outside of the elevator car as quickly as possible.

Second Embodiment

An emergency elevator according to a second embodiment of the present invention will be described with reference to FIGS. 9 to 13.

The emergency elevator according to the second embodiment of the present invention further includes a refractory door 170 disposed in front of the platform doors 130 described in the first embodiment.

When a fire is not completely suppressed while rescuing all the people, the emergency elevator has to be able to safely pass through the fire-occurring floor and reach the upper floors above the fire-occurring floor in order to rescue a large number of people on the upper floors.

However, when the outer door of the elevator on the fire-occurring floor is destroyed by the flame or heat, and when the noxious gas is introduced into the elevator car, it is substantially impossible to operate the emergency elevator.

The second embodiment of the present invention is intended to solve such a problem. The platform doorway and the door of the elevator car are protected by the refractory door 170 to ensure that the emergency elevator is normally operated.

Preferably, the refractory door 170 is configured to be automatically closed as a fire is detected by a fire detection unit 200.

Although not shown in the drawings, a fireproof door may be further provided in front of the platform doors 130 in addition to the refractory door 170.

As shown in FIGS. 9 to 13, the emergency elevator according to the second embodiment of the present invention further includes a fire detection unit 200 for detecting a fire occurring on each floor, and a refractory door 170 rotatably installed in a platform doorway 180 so as to close the platform doorway 180 in response to a signal from the fire detection unit 200 and provided with a heat-resistant packing 170b.

The refractory door 170 is preferably a double door rotatably installed on both side walls and configured to close the platform doorway 180 by being coupled in a zigzag form at the center when a fire occurs.

It is preferable that the refractory door 170 is formed in a hinged manner and is normally accommodated inside the wall finish line 190a of wall 190 and that the surface of the refractory door 170 is identical with the wall finish line 190a.

Accordingly, even if the refractory door 170 is additionally installed, it is possible to prevent the aesthetic appearance from being deteriorated.

Switches for operating the refractory door 170 are installed on the inside of the platform doorway 180 and on the elevator outer wall. Each of the switches is configured to independently operate the refractory door 170.

As a result, when a fire occurs, the refractory door 170 is opened using the switch on the outer wall of the elevator so as to enable a person to evacuate through the platform doorway 180. After the evacuation is completed, the refractory door 170 is closed to prevent flames, smoke and noxious gases from entering the platform doorway 180.

The heat-resistant packing provided on the platform doors 130 prevents the harmful gas or smoke introduced into the platform doorway 180 from entering the elevator passage.

Heat-resistant packing 130b or 170b capable of blocking a harmful gas and smoke is also installed in the door rim 130a and the door frame 170a so as to prevent the harmful gas and smoke generated during a fire from entering the elevator passage through the gap between the door rim 130a and the door frame 170a.

Figure 12:
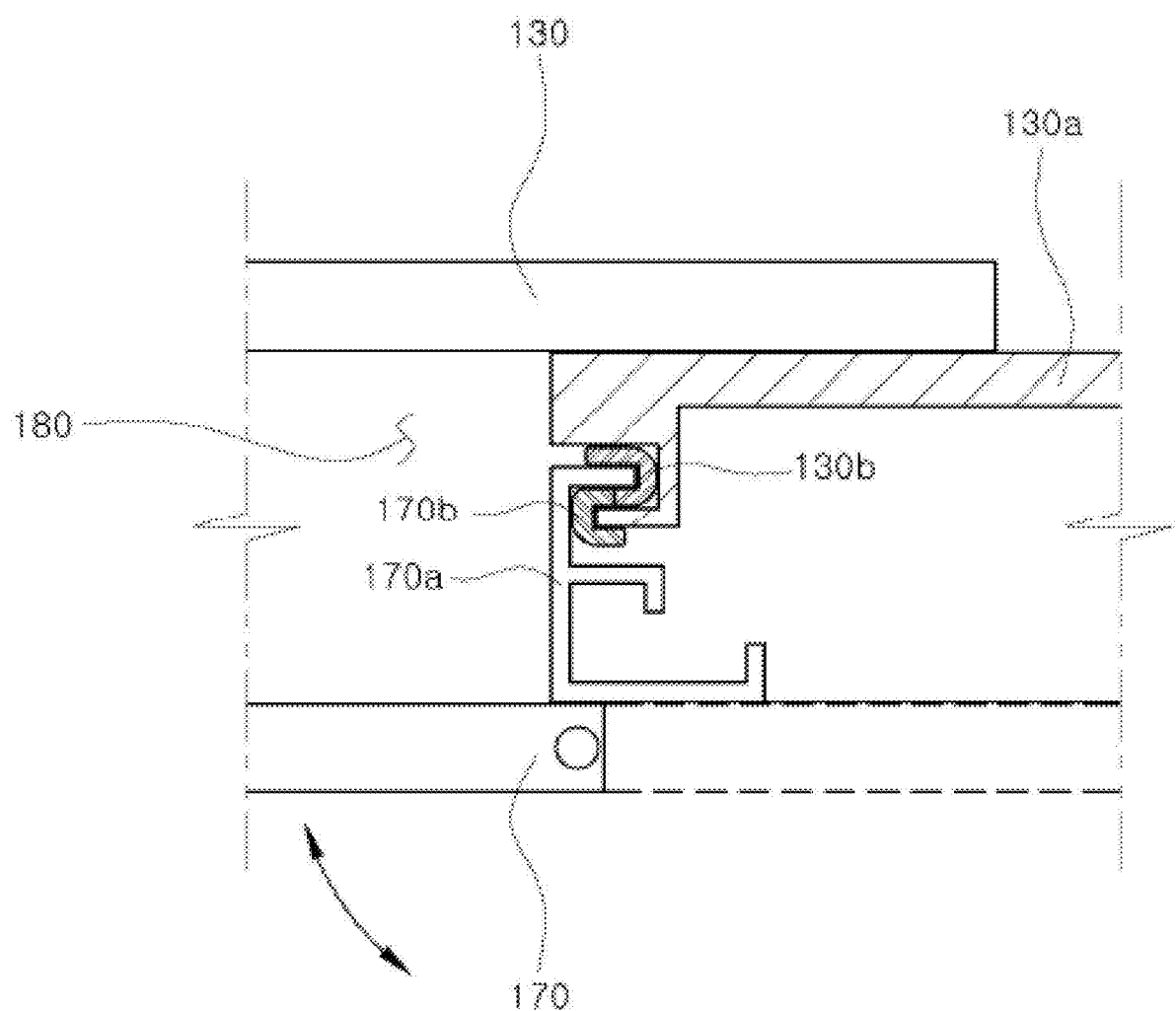
FIG. 12 is a sectional plan view of a door rim and a door frame according to the second embodiment of the present invention.

That is, as shown in FIG. 12, the door rim 130a and the door frame 170a provided on both sidewalls of the platform doorway 180 are engaged in a zigzag form on the left, right and upper sides of the platform doorway. Heat-resistant packing 130b or 170b is installed at the ends of the door frame 170a and the door rim 130a.

In addition, a gap sealing member 160 is provided at a lower portion of the platform doors 130 so as to prevent a harmful gas or smoke from entering the elevator passage through the lower portion of the platform doors 130.

Figure 13:
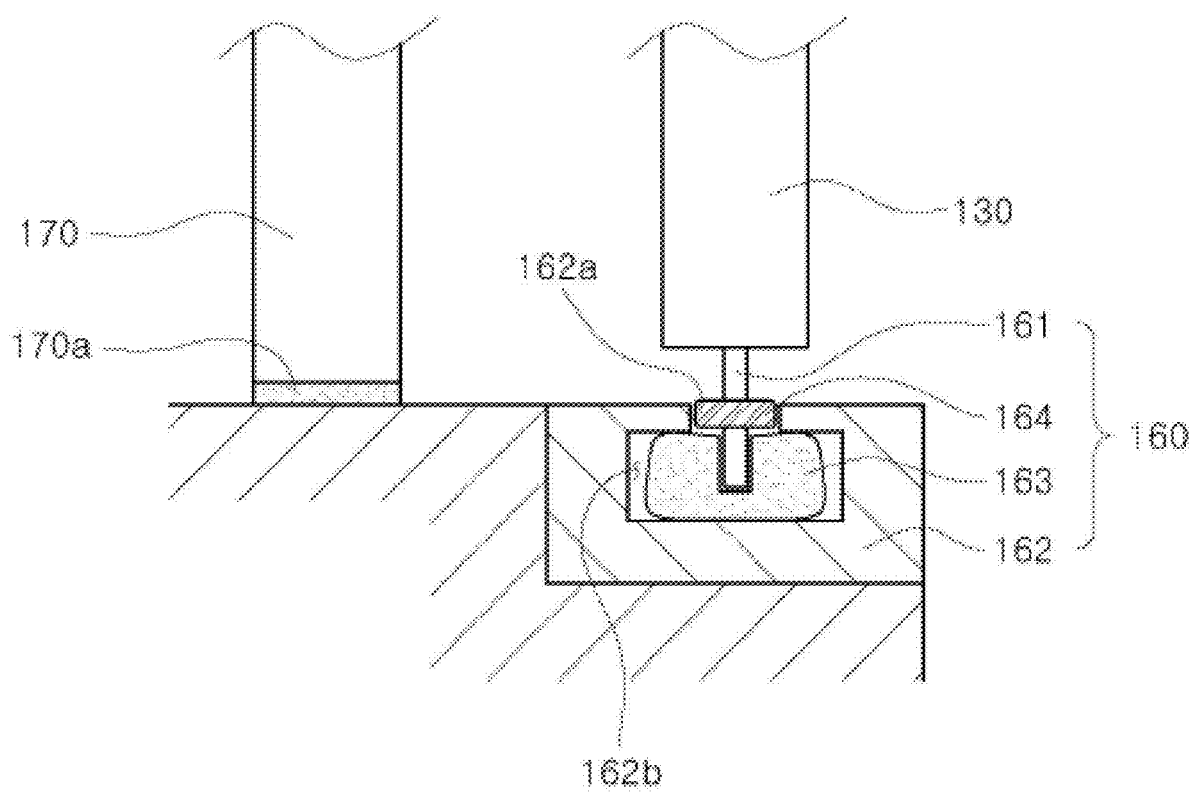
FIG. 13 is a sectional side view of a gap sealing member according to the second embodiment of the present invention.

As shown in FIG. 13, the gap sealing member 160 includes a metal shielding plate 161 installed along the longitudinal direction at the lower portion of the platform doors 130, a lower door rim 162 installed at the lower portion of the platform doors 130 and provided with an entrance portion 162a through which the metal shielding plate 161 passes and an accommodation space 162b having a predetermined size, a heat-resistant packing 163 installed in the accommodation space 162b and configured to make contact with the lower portion of the metal shielding plate 161 at its upper end, and a door guide shoe 164 installed in the metal shielding plate 161 so as to make contact with the entrance portion 162a of the lower door rim 162 and configured to guide the movement of the platform doors 130.

When a fire occurs in a high-rise building, the fire detection unit 200 detects the fire, and the refractory door 170 is closed so as to prevent flames, smoke, noxious gases and the like from entering the platform doorway 180.

At this time, the person failed to evacuate may press the switch on the outside wall of the platform to open the refractory door 170. After evacuating to the platform doorway 180, the person may close the refractory door 170 using the switch of the platform doorway 180.

In the case where the refractory door 170 is further installed, the refractory door 170 is positioned in front of the platform doors 130.

When the refractory door 170 is closed as described above, flames, smoke and noxious gases are prevented from entering the platform doorway 180 due to the heat-resistant packing 170b installed on the refractory door 170. Therefore, the person evacuated to the platform doorway 180 can be safely evacuated through the elevator car 100.

Other configurations are the same as those of the emergency elevator according to the first embodiment of the present invention.

While some preferred embodiments of the present invention have been described above, the present invention is not limited to these embodiments. It is to be understood that various changes and modifications may be made without departing from the scope of the invention defined in the claims.

What is claimed is:

1. An emergency elevator, comprising:
   a door frame installed on upper, left and right sides of an entrance of an elevator platform;
   an elevator car configured to vertically move along an elevator passage and to stop in the elevator platform and provided with a pair of elevator doors configured to be slidingly opened and closed;
   a pair of platform doors in the door frame so as to be slidingly opened and closed in association with the elevator doors;
   a lower frame on a lower side of the entrance of the elevator platform and configured to slidably support the platform doors;
   an upper door rim on an upper side of the platform doors;
   a side door rim vertically installed at a lateral end of the platform doors;
   an oxygen supply device configured to supply oxygen to a patient in the elevator car, the oxygen supply device including an oxygen generator unit disposed at an upper portion of the elevator car, an oxygen storage container configured to store oxygen, and a length-adjustable oxygen mask unit disposed inside the elevator car and connected to the oxygen storage container so as to supply oxygen to the patient;
   an emergency ventilation device configured to supply a purified air into the elevator car and to discharge a contaminated air, the emergency ventilation device including an air purifying device installed at the upper portion of the elevator car, a blowing duct configured to connect the air purifying device to a blowing hole formed in an upper plate of the elevator car and to supply the purified air into the elevator car, an air intake duct configured to connect the air purifying device to an air intake hole formed at a side lower end of the elevator car and to draw the contaminated air in the elevator car to supply the contaminated air to the air purifying device, and a sterilizing/disinfecting device provided on one side of the air purifying device and configured to remove and sterilize noxious substances in an air;
a filter device provided in the blowing duct so as to remove harmful substances introduced into the elevator car;
an upper sealing member between the upper door frame and the upper door rim;
a side sealing member between the door frame installed on left and right sides and the side door rim;
a lower sealing member between the platform doors and the lower frame;
a lighting device provided outside the elevator car so as to enable a person to safely escape from the elevator car; and
an emergency escape device configured to enable the person to escape when the elevator car is stopped,
wherein the emergency escape device includes an upper hatch openably installed at the upper portion of the elevator car so as to enable the person to escape to an upper side of the elevator car, a lower hatch openably installed at a bottom of the elevator car so as to enable the person to escape to a lower side of the elevator car, a slow descent device installed on a horizontal member connecting a pair of vertical car frames, and a safety bar foldably installed inside the elevator car so as to enable the person to grip the safety bar when escaping to the lower side of the elevator car.

2. The emergency elevator of claim 1, further comprising:
an emergency medical instrument and a first-aid kit provided inside the elevator car and removably stored in an inner wall of the elevator car.

3. The emergency elevator of claim 1, further comprising:
a sprinkler installed at the upper portion of the elevator car; and
a cleaning device removably stored in an inner wall of the elevator car so as to supply water stored in a water tank.

4. The emergency elevator of claim 1, wherein the filter device provided in the blowing duct includes a HEPA filter and an ULPA filter.

5. The emergency elevator of claim 1, further comprising:
an ultraviolet lamp configured to irradiate ultraviolet rays to an air passing through the blowing hole.

6. The emergency elevator of claim 1, wherein the filter device includes an activated charcoal filter.

7. The emergency elevator of claim 1, wherein the filter device includes a silver nano filter.

8. The emergency elevator of claim 1, wherein the air intake hole is closed and air amount blowing from the blowing hole is increased when elevator car is stopped on a fire-occurring floor and elevator door is opened.

9. The emergency elevator of claim 1, further comprising:
a sealing member provided on each of coupling surfaces of the platform doors.

10. The emergency elevator of claim 1, wherein the upper sealing member is inserted into a transverse accommodation portion formed in the upper door rim so as to make close contact with the upper door frame, and
so that the upper sealing member is inserted into an insertion groove formed in the upper door frame so as to make close contact with an inner surface of each of the platform doors.

11. The emergency elevator of claim 1, wherein the side sealing member is inserted into a vertical accommodation portion formed in the side door rim so as to make close contact with the side door frame, and
so that the side sealing member is inserted into an insertion groove formed in the side door frame so as to make close contact with an outer surface of each of the platform doors.

12. The emergency elevator of claim 1, wherein the lower sealing member attaches to each side surface of a metal shielding plate installed at a lower portion of each of the platform doors, and an accommodation space is formed in the lower frame to accommodate the lower sealing member attached to each side surface of the metal shielding plate.

13. The emergency elevator of claim 1, wherein each of the sealing members includes a graphite bar and a graphite plate.

14. The emergency elevator of claim 1, further comprising:
a fire detection device configured to detect a fire occurring on each floor;
a refractory door rotatably installed in a platform doorway and configured to close the platform doorway; and
a receiving device connected to operate the refractory door in response to a signal transmitted from the fire detection device.

15. The emergency elevator of claim 14, wherein the refractory door includes a pair of rotary doors rotatably installed on side walls of the platform doorway and configured to engage with each other to close the platform doorway.

16. The emergency elevator of claim 14, wherein the refractory door includes a sliding door configured to be slidably opened and closed so that, when closed, the sliding door is accommodated inside a wall defining the platform doorway.

17. The emergency elevator of claim 14, further comprising:
a gap sealing member provided at a lower portion of each of the platform doors,
wherein the gap sealing member includes a metal shielding plate installed at the lower portion of each of the platform doors along a longitudinal direction, a lower door rim installed at the lower portion of each of the platform doors and provided with an entrance portion through which the metal shielding plate passes and an accommodation space having a predetermined size, a heat-resistant packing installed in the accommodation space and configured to make contact with a lower portion of the metal shielding plate at an upper end thereof, and a door guide shoe installed in the metal shielding plate so as to make contact with the entrance portion of the lower door rim and configured to guide movement of the platform doors.

* * * * *